United States Patent
Terrien et al.

(10) Patent No.: US 11,491,440 B2
(45) Date of Patent: Nov. 8, 2022

(54) MEMBRANE NITROGEN REJECTION PROCESS AND SYSTEM

(71) Applicant: Air Liquide Advanced Technologies US LLC, Houston, TX (US)

(72) Inventors: Paul Terrien, Syracuse, NY (US); Alex Augustine, King of Prussia, PA (US); Kevin Weatherford, Houston, TX (US); Yong Ding, Waban, MA (US)

(73) Assignee: Air Liquide Advanced Technologies U.S. LLC, Houston, TX (US)

( * ) Notice: Subject to any disclaimer, the term of this patent is extended or adjusted under 35 U.S.C. 154(b) by 72 days.

(21) Appl. No.: 16/702,010

(22) Filed: Dec. 3, 2019

(65) Prior Publication Data
US 2021/0162337 A1 Jun. 3, 2021

(51) Int. Cl.
*B01D 53/22* (2006.01)
*B01D 71/70* (2006.01)
*C07C 7/144* (2006.01)
*C10L 3/10* (2006.01)

(52) U.S. Cl.
CPC ........... *B01D 53/226* (2013.01); *B01D 71/70* (2013.01); *C07C 7/144* (2013.01); *C10L 3/105* (2013.01); *C10L 2290/548* (2013.01)

(58) Field of Classification Search
None
See application file for complete search history.

(56) References Cited

U.S. PATENT DOCUMENTS

| | | | |
|---|---|---|---|
| 5,264,171 A * | 11/1993 | Prasad | B01D 53/22 264/103 |
| 5,378,263 A * | 1/1995 | Prasad | B01D 53/226 95/45 |
| 5,647,227 A | 7/1997 | Lokhandwala | |
| 5,669,958 A | 9/1997 | Baker et al. | |
| 5,964,923 A | 10/1999 | Lokhandwala | |
| 6,035,641 A | 3/2000 | Lokhandwala | |
| 6,425,267 B1 * | 7/2002 | Baker | B01D 53/228 62/624 |
| 6,630,011 B1 | 10/2003 | Baker et al. | |
| 2007/0125537 A1 | 6/2007 | Lokhandwala et al. | |

(Continued)

FOREIGN PATENT DOCUMENTS

| EP | 0 778 068 | 6/1997 |
|---|---|---|
| EP | 0 862 937 | 9/1998 |

OTHER PUBLICATIONS

Lokhandwala, et al., "Membrane separation of nitrogen from natural gas: A case study from membrane synthesis to commercial deployment," Journal of Membrane Science, 346, (2010), pp. 270-279.

(Continued)

*Primary Examiner* — Jason M Greene
(74) *Attorney, Agent, or Firm* — Christopher J. Cronin

(57) ABSTRACT

A feed containing methane and nitrogen gas is processed in a three-stage membrane system, each stage of which is selective for methane over nitrogen. The methane enriched permeate from the first stage is removed as product gas. The methane-depleted residue from the second stage is purified in second and third cascaded stages to provide second and third permeates and second and third residues. The third stage permeate is recycled to the feed.

12 Claims, 2 Drawing Sheets

(56) References Cited

U.S. PATENT DOCUMENTS

2010/0077796 A1 4/2010 Gadre et al.
2017/0304769 A1 10/2017 Bigeard et al.
2019/0201838 A1 7/2019 Bikson
2019/0321780 A1 10/2019 Bikson et al.

OTHER PUBLICATIONS

Pathare, et al., "Design of membrane cascades for gas separation," Journal of Membrane Science, 364, (2010), pp. 263-277.
International Search Report and Written Opinion for PCT/US2020/062667, dated Feb. 2, 2021.
International Search Report and Written Opinion for PCT/US2020/062669, dated Feb. 2, 2021.

* cited by examiner

Table 2: Compositions of streams

| Label | 17 | 24 | 22 | 38 | 25 | 44 | 42 | 54 | 64 | 62 | 72 | 46 |
|---|---|---|---|---|---|---|---|---|---|---|---|---|
| A | 1.00 | 1.00 | 1.00 | 1.00 | 1.00 | 1.00 | 1.00 | 1.00 | 1.00 | 1.00 | 1.00 | 1.00 |
| B | 120 | 64 | 97 | 120 | 90 | 40 | 69 | 120 | 68.69 | 98.56 | 120.00 | 50.07 |
| C | 1,100 | 1,095 | 15 | 770 | 1,090 | 1,085 | 50 | 1,100 | 1,100.00 | 50.00 | 1,100.00 | 1,085.00 |
| D | 29.01 | 9.59 | 19.42 | 19.42 | 9.59 | 3.57 | 6.02 | 6.02 | 2.01 | 4.01 | 4.01 | 5.58 |
| E | 54,500 | 18,431 | 36,070 | 36,070 | 18,431 | 7,306 | 11,125 | 11,125 | 3,856 | 7,269 | 7,269 | 11,161 |
| F | - | - | -170 | - | - | - | -196 | - | - | -191 | - | - |
| G | - | - | - | - | - | - | - | - | - | - | - | - |
| H | 964 | 887 | 1,001 | 1,001 | 887 | 786 | 947 | 947 | 884 | 979 | 979 | 821 |
| I | 0.06% | 0.01% | 0.09% | 0.09% | 0.01% | 0.00% | 0.01% | 0.01% | 0.00% | 0.02% | 0.02% | 0.00% |
| J | 5.75% | 11.78% | 2.77% | 2.77% | 11.78% | 21.67% | 5.92% | 5.92% | 11.92% | 2.91% | 2.91% | 18.16% |
| K | 91.77% | 87.83% | 93.71% | 93.71% | 87.83% | 78.27% | 93.50% | 93.50% | 87.98% | 96.27% | 96.27% | 81.77% |
| L | 2.27% | 0.37% | 3.21% | 3.21% | 0.37% | 0.07% | 0.56% | 0.56% | 0.10% | 0.79% | 0.79% | 0.08% |
| M | 0.14% | 0.01% | 0.20% | 0.20% | 0.01% | 0.00% | 0.01% | 0.01% | 0.00% | 0.02% | 0.02% | 0.00% |
| N | 0.00% | 0.00% | 0.00% | 0.00% | 0.00% | 0.00% | 0.00% | 0.00% | 0.00% | 0.00% | 0.00% | 0.00% |
| O | 0.00% | 0.00% | 0.01% | 0.01% | 0.00% | 0.00% | 0.00% | 0.00% | 0.00% | 0.00% | 0.00% | 0.00% |

FIG 2

US 11,491,440 B2

MEMBRANE NITROGEN REJECTION PROCESS AND SYSTEM

INCORPORATION BY REFERENCE

This application is related to U.S. patent application entitled "Cold Membrane Nitrogen Rejection Process and System", filed on an even date under attorney docket number 2019P00259US. The afore-mentioned application is incorporated herein by this reference in its entirety.

BACKGROUND OF THE INVENTION

A component that can often be found in biogas or in natural gas is nitrogen ($N_2$). While not presenting a major problem for some applications, nitrogen generally reduces the heating value of natural gas. Although small amounts of this inert gas can often be tolerated, natural gas containing levels higher than 4-5% vol of $N_2$ is typically unacceptable.

Various approaches can be employed to reduce nitrogen levels. The most common rejection technology relies on cryogenic separation. While relatively efficient, the cryogenic removal of $N_2$ can requires large equipment and balance of plant, rendering this approach uneconomical in some situations, particularly for small flow rates.

Membrane separation is a very cost effective and simple way to separate gases. Separating $CH_4$ and $N_2$, however, has proved to be challenging. Some rubbery membranes such as poly(dimethylsiloxane) and derivatives, poly(methyloctylsiloxane, and polyamide-polyether copolymer can achieve a $CH_4/N_2$ selectivity of 2 to 4. Generally, this is not found satisfactory for generating a high product purity and good product recovery.

It is known that the $CH_4/N_2$ selectivity can be increased at low temperatures (below 0° C.). U.S. Pat. No. 5,669,958 to Baker et al., for example, describes operating polysiloxane membranes at temperatures as low as −50° C., for a $CH_4/N_2$ selectivity of up to 6, to remove $N_2$ and generate pipeline quality gas with high methane recovery. The method described in this patent utilizes a turbo-expander to supply the cooling required by the process.

In U.S. Pat. No. 6,425,267 to Baker et al., a two- or three-stage membrane process for $CH_4/N_2$ separation is conducted at an intermediate low temperature such that high $CH_4$ recovery is achieved without the use of external refrigeration or turbo-expansion. The incoming feed gas is cooled to a sub-ambient temperature by a combination of residue and permeate streams; the cooling is generated by the Joule-Thomson effect of the membranes.

U.S. Pat. No. 6,630,011 B1 to Baker et al. describes a separation of $CH_4$ and $N_2$ that uses a multi-stage membrane process to achieve high methane recovery. The process is optionally operated fully or partially at low temperature for enhanced performance.

In a publication by K. A. Lokhandwala et al, several two stage and three stage arrangement membrane process for nitrogen removal were discussed, see K. A. Lokhandwala et al., J. Membrane Sci., vol. 346, page 270-279, titled "Membrane separation of nitrogen from natural gas: A case study from membrane synthesis to commercial deployment".

In a publication by R. Pathare and R. Agrawal., all five possible different membrane arrangement for two stage or three stage design are listed based on membrane cascade schemes, see R. Pathare and R. Agrawal, J. Membrane Sci., vol. 364, page 263-267, titled "Design of membrane cascades for gas separation".

SUMMARY OF THE INVENTION

One problem associated with many existing approaches for the $CH_4/N_2$ separation relates to the cost effectiveness of reaching the lowest membrane operating temperature possible. Other difficulties are raised by the numerous heat exchangers and temperature limitations imposed in many existing techniques.

Complicated and equipment intensive schemes, often currently necessary to separate $CH_4/N_2$, tend to raise capital and operational costs and can affect the overall economics of natural gas or biogas processing. This becomes particularly relevant when handling relatively small volumes, when wishing to produce pipeline quality gas from feeds that contain relatively modest levels of nitrogen gas (e.g., up to about 10 mol %, or when the ratio between a feed nitrogen concentration and a product nitrogen concentration is lower than 4.

Thus, a need continues to exist for $N_2$ rejection technologies that can reach sufficiently low $N_2$ levels in processing natural gas or biogas. A need also exists for approaches that address at least some of the problems discussed above. For example, it is desirable to conduct an effective $CH_4/N_2$ while reducing or eliminating the need for cooling the feed stream, a requirement often encountered with existing technologies. Simplified and less expensive arrangements for handling mixtures that contain relatively modest amounts of nitrogen gas are desirable as well.

Generally, the invention relates to multi-stage membrane separation techniques for reducing $N_2$ levels in a fluid stream comprising, consisting essentially of or consisting of methane and nitrogen gas (also referred to herein simply as "nitrogen" or "$N_2$"). In many embodiments, cooling the feed stream introduced to the first membrane stage is not necessary, but rather optional, and the system and process described herein can handle feeds at nonspecific temperatures, including feeds at temperatures above 0° C., such as, for instance, feeds at ambient (room) temperature.

The invention may include any one or more of the following aspects.

The invention features a three-stage membrane separation process in which a feed containing methane and nitrogen is processed in a first membrane stage to produce a first permeate and a first residue. The first permeate, rich in $CH_4$ and $N_2$-depleted, can undergo further processing (e.g., the removal of condensable material and/or pressure modifications) and represents the product gas, having a pipeline gas quality, for example.

The first residue is directed to a second stage, a methane recovery stage, to produce a second permeate ($CH_4$-enriched) and a second residue, rich in $N_2$. The second permeate is purified in a third stage to obtain a third permeate (further enriched in $CH_4$) and a third residue. The third permeate can be used as a recyclable stream and can be directed back to the feed. The $N_2$-enriched second and third residues can be handled as waste or used in a different operation, e.g., one that requires nitrogen. For instance, the $N_2$-rich fraction can be utilized to regenerate an adsorbent bed.

The invention features a system that includes: a first membrane stage for processing a feed to produce a first permeate and a first residue; an arrangement for collecting (withdrawing from the system) the first permeate as a methane-rich product gas; a second membrane stage for recovering methane from the first residue to produce a second permeate and a second residue; a third membrane stage for purifying the second permeate to produce a third permeate; an arrangement for recycling the third permeate back to the feed; and a heat exchanger for modifying the temperature of the first residue. In many implementations, the first membrane stage is configured to process a feed containing up to about 8 mol % nitrogen gas without cooling the feed.

The invention features a membrane separation process that includes the following steps. A feed containing methane and nitrogen gas is processed in a first membrane stage to produce a first permeate and a first residue, the feed having an $N_2$ content (in vol %), $F_{nitrogen}$. The first permeate is removed as a methane-rich product, the methane-rich product having an $N_2$ content (in vol %), $P_{nitrogen}$. The first residue is processed in a second membrane stage to recover additional methane in a second permeate. The second permeate is processed in a third membrane stage to obtain a third permeate. The third permeate is recycled by combining it with the feed.

The invention features a membrane separation system, comprising: a first membrane stage for processing a nitrogen and methane-containing feed to produce a first permeate product gas and a first residue, the first membrane stage comprising membranes selective for methane over nitrogen, a feed inlet, a permeate outlet, and a residue outlet; a second membrane stage for recovering methane from the first residue to produce a second permeate and a second residue, the second membrane stage comprising membranes selective for methane over nitrogen, a feed inlet in downstream fluid communication with the permeate outlet of the first membrane stage, a permeate outlet, and a residue outlet; a third membrane stage for purifying the second permeate to produce a third permeate, the third membrane stage comprising membranes selective for methane over nitrogen, a feed inlet in downstream flow communication with the residue outlet of the second membrane stage, a permeate outlet, and a residue outlet; and a conduit for recycling the third permeate back to the feed in downstream fluid communication with the permeate outlet of the third membrane stage and in upstream flow communication with the feed inlet of the first membrane stage.

A temperature of the first residue adjusted.

One or more of the first, second and third permeate is compressed

Each of the first, second, and third permeates is compressed.

At least one of a second residue, obtained from the second membrane stage, and a third residue, obtained from the third membrane stage, is removed from the process as a nitrogen-rich fraction.

The first membrane stage is operated at a stage cut within the range of from about 50% to about 95%.

The first membrane stage is operated in radial cross flow mode

At least one of the first, second and third membrane stages comprises a membrane having a separation layer that includes a copolymer of dimethylsiloxane.

The first residue is passed through a heat exchanger.

$F_{nitrogen}$ is no more than 12 vol %.

$P_{nitrogen}$ is less than 3 vol %.

Said system does not include any heat exchanger for cooling the feed.

The membrane separation system further comprises a heat exchanger for modifying the temperature of the first residue.

A ratio of $F_{nitrogen}:P_{nitrogen}$ is less than 4

The membrane separation system is configured to produce a first permeate having a nitrogen content that is less than 4 times a nitrogen content of the feed The system further comprises a first compressor for raising a pressure of the first permeate, a second compressor for raising a pressure of the second permeate; and/or a third compressor for raising a pressure of the third permeate.

Practicing the invention is particularly useful in handling $CH_4$-containing mixtures that are characterized by relatively modest levels (e.g., about 8 mol % or less) of nitrogen gas. The multi-stage separation approach described herein offers a simplified solution for generating a product characterized by a good or acceptable methane purity (e.g., containing no more than about 3-4 mol % $N_2$), coupled with an advantageous arrangement for methane recovery. While the product represents or is derived from the first permeate, the second and third stage can be used to generate a recyclable stream with a methane content at or near the methane content of the feed, thus reducing or eliminating the possibility of introducing additional $N_2$ to the feed.

In contrast to many existing techniques, the process and system described herein do not require cooling the feed being passed through the first membrane stage. In fact, the cooling and heating schemes employed are advantageously minimized. In some cases, the system only includes one heat exchanger and this heat exchanger is used only to modify the temperature of the first residue, e.g., to mitigate the Joule-Thompson expansion cooling taking place in the first membrane stage.

The above and other features of the invention including various details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 2 is a chart of various properties of a computer simulation of the invention.

DETAILED DESCRIPTION OF THE PREFERRED EMBODIMENTS

Figure 1:
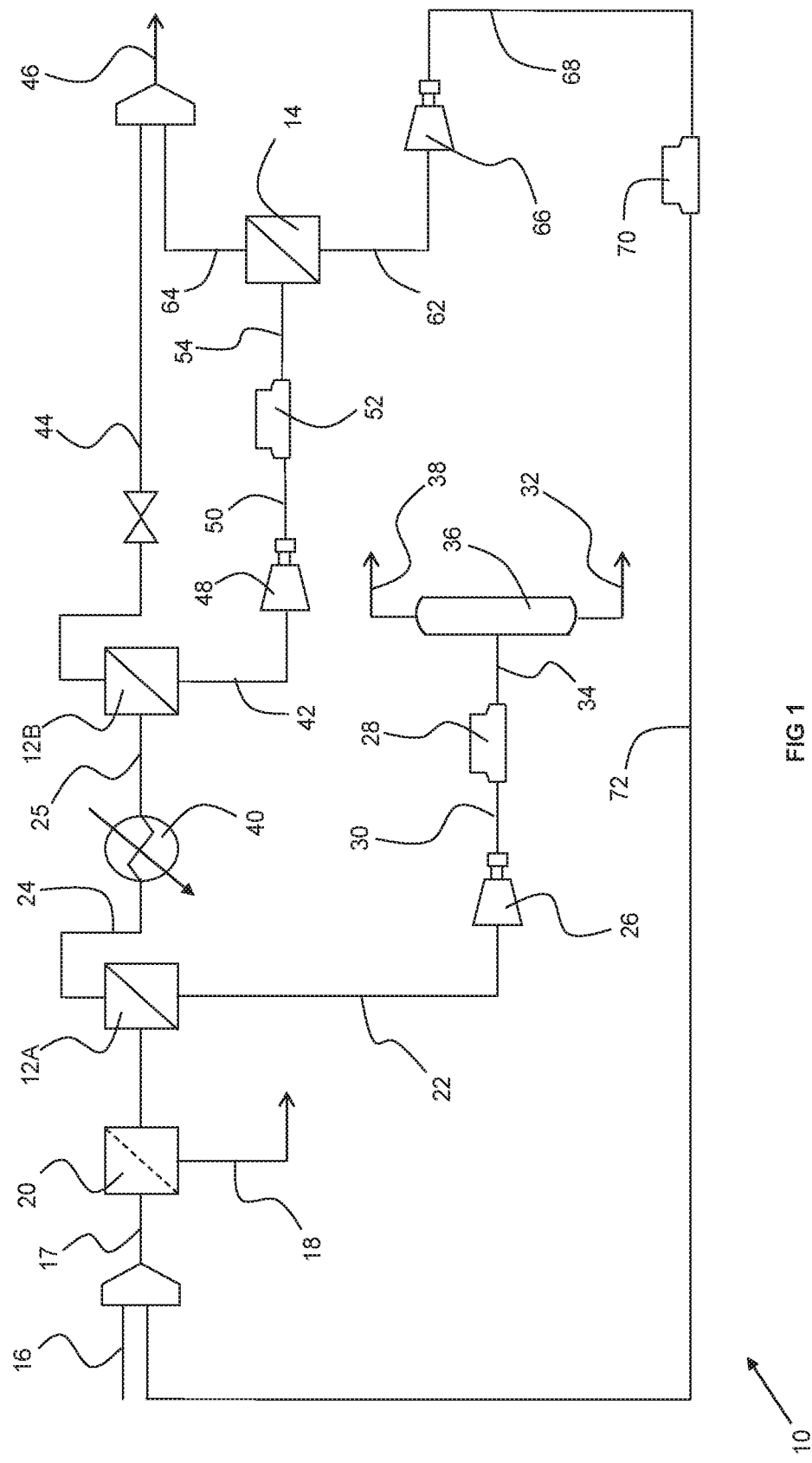
FIG. 1 is a process diagram of a multi-stage $CH_4/N_2$ membrane separation according to embodiments of the invention.

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

It will be understood that although terms such as "first" and "second" are used herein to describe various elements, these elements should not be limited by these terms. These terms are only used to distinguish one element from another element.

Thus, an element discussed below could be termed a second element, and similarly, a second element may be termed a first element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The invention generally relates to a multi-stage membrane separation process and system. In specific implementations, the separation process involves three membrane separation stages, also referred to as "membrane stages" or simply "stages" and is directed to removing (also referred to as "rejecting") $N_2$ from a gas mixture. Each stage may include one or more gas separation membranes.

The mixture can consist of, consist essentially of or comprise $CH_4$ and $N_2$. In many embodiments, the mixture being handled includes no more than about 10 mol % $N_2$.

Other components that can be present, in addition to $CH_4$ and $N_2$, include higher hydrocarbons (e.g., ethane, propane, butane, pentane, hexane, etc.), carbon dioxide ($CO_2$), carbon monoxide (CO), hydrogen gas ($H_2$), helium (He), hydrogen sulfide ($H_2S$, ammonia ($NH_3$), water vapor, etc. Water can be present in any amounts. Feeds that contain particulate matter can be purified using a suitable filtration device, for example.

Specific examples of mixtures that comprise $CH_4$ and $N_2$ include natural gas (such as but not limited to traditional natural gas, shale gas, associated gas) and biogas (such as but not limited to gas from digesters, landfills, etc.). In biogas, $N_2/CH_4$ ratio can range typically from 0-1% mol (in which case no particular nitrogen removal treatment is required) to 10% mol or more. Natural gas usually contains very small amounts of nitrogen compatible with pipeline specifications but some natural gas fields contain higher amount of nitrogen ranging from a few percent up to close to 100% in some extreme cases. In some cases, the biogas and natural gas field contain only a limited amount of nitrogen (typically from 3-4% mol up to 10-15% mol).

The membranes are selected based on their performance for the desired separation, that of $CH_4$ and $N_2$, for instance. Possible membranes that can be employed are described in U.S. Pat. Nos. 5,669,958 and 6,630,011B1. Membranes having the potential to effect the $CH_4$—$N_2$ separation often include rubbery membranes such as those having a rubbery separation layer. Some potential examples of materials that can be employed for the separation layer include poly (dimethyl siloxane) (PDMS), e.g., homopolymers of dimethylsiloxane, and copolymers of dimethyl siloxane with methylethyl siloxane, methyl propyl siloxane, methyl butyl siloxane, methyl pentylsiloxane, methyl hexyl siloane, methyloxtyl siloane, methyl phenyl siloxane. The rubbery material can include block copolymers of dimethylsiloxane or methyloctylsiloxane with polyarylethers, polyamides, polyesters, polyketones, polyimides or block copolymers of dimethyl siloxanes or methyl octyl siloxane with silicates. Another possible material is a ladder-type silicone block copolymer with a general formula of:

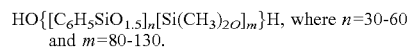

Many implementations described herein utilize a rubbery type membrane that preferentially permeates $CH_4$, with the residue (also referred to as "retentate") representing the $N_2$-rich fraction. Factors such as the specific membrane material, flat sheet, hollow fiber, etc. configuration, performance characteristics, and so forth, can be selected according to the process to be conducted, size of the operation, feed composition, feed properties, and so forth.

To obtain a product of a specified nitrogen content, characteristics of the membranes employed (selectivity, operating conditions, etc.) can influence the type of mixture that potentially could be handled. In one example, the system and/or process described herein is used to reduce the $N_2$ level in the mixture from about 6% mol to about 3% mol.

Many aspects of the invention involve a three-stage separation process or system in which the membrane material and/or membrane attributes in the three membrane stages employed are the same or different. Other aspects utilize membranes that are individually tailored. Thus, two or all three stages may utilize different membrane materials or membrane characteristics.

In one embodiment, a feed is processed in a first membrane stage to produce a first permeate and a first residue. The first permeate has a methane content characteristic of the product gas. Optionally, the first permeate can be compressed and/or stripped of condensables before being collected or removed from the process as the product fraction.

The first residue is processed in a second membrane stage, employed to recover additional methane. The second permeate generated in the second stage is processed in a third stage to further purify the recovered methane and produce a third permeate that can be recycled back to the feed. Stated differently, the $CH_4$-rich recyclable stream can be thought of as being made up of fluids derived from the second permeate. As used herein, the terms "fluids derived from a permeate" or "fluids derived from a residue" refer to or include any fluid that is obtained, directly or indirectly, after splitting or after treatment steps, from the permeate or residue, such as, for example:

1) a fraction of the initial fluid;
2) the initial fluid or a fraction thereof after a change in conditions (pressure, temperature, vapor fraction);

3) the result of a phase separation after a phase change (for instance if the stream is partially condensed and only the gas or a part of the gas is used);
4) the result of a membrane separation (for instance only the residue or a part of the residue of a membrane treated the initial fluid).

The second and the third residues represent $N_2$-rich fractions that can be handled as waste gas or can be employed for purging, blanketing or other operations.

As best shown in FIG. 1, a three-stage nitrogen rejection (also referred to herein as a "nitrogen removal") unit (NRU) 10 includes membrane separation stages 12A, 12B and 14.

A mixture containing, for example, at least methane and nitrogen, is supplied to the system as feed 16. Typically, this feed is at a temperature that is above 0° C. In many cases, feed 16 is at or above ambient (room) temperature. The feed can contain nitrogen in an amount no greater than about 10 mol %, e.g., in an amount no greater than about 9, 8, 7, 6 or 5 mol %, and can enter system 10 in a compressed state (e.g., 50 to 2000 pounds per square inch gauge (psig)).

Feed 16 and recycle stream 72 are combined as first stage inlet stream 17 and optionally subjected to a filtration step to remove particulates 18 that may be present in the feed, using, for instance, filter separator 20. The filter separator can be configured to remove particles having a size higher than 1 micron.

The first stage inlet stream 17, optionally purified in filter separator 20, is processed in stage 12A to produce permeate 22 (rich in $CH_4$,) and residue 24 (rich in $N_2$).

Specific embodiments employ membrane in stages 12A, 12B, 14 that are selected to offer a sufficiently high $CH_4/N_2$ selectivity, at ambient temperature, to achieve a desired product purity. In one implementation, the membranes includes a separation layer made of homopolymer of dimethylsiloxane. In another implementation, the membranes may have a separation layer that includes a homopolymer of methyloctylsiloxane, a block copolymer of dimethylsiloxane, or a ladder-type silicone block copolymer with a general formula of:

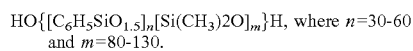
and $m=80\text{-}130$.

Stage 12A can be configured to operate at a stage cut (i.e., the ratio of the permeate flow rate to the feed flow rate) that is higher than about 50%, e.g., higher than 55%, 60%, 65%, 70%, 80%, or even up to about 90%. The membrane(s) of stage 12A can be operated in radial cross flow mode or counter current flow mode, preferably in radial cross flow mode.

Streams that emerge from a membrane stage can have a reduced pressure and can be compressed using a compressor or another suitable device. For instance, the pressure of permeate 22 can be boosted in compressor 26.

From compressor 26, the permeate fraction, having a pressure that is, for instance, within the range of from about 200 to about 1400 psig, e.g., about 1200 psig, is directed to gas aftercooler 28 as stream 30. Condensates (such as, for instance, water) and/or liquid natural gas fractions (e.g., heavier hydrocarbons, LPGs, etc.) 32 can be removed from stream 34, in coalescing filter 36. Stream 38 exits the coalescing filter as the methane rich product gas and is removed (also referred to herein as "collected") from the system. In many implementations, stream 38 is a pipeline quality gas stream with an $N_2$ content of less than 3-5 vol %), from feed compositions that have a $N_2$ content of less than 10 vol %.

Residue 24 ($N_2$-rich and depleted in $CH_4$) will typically exit stage 12A at temperatures that are lower, e.g., by 5-50° C., than the feed temperature, due to the Joule-Thomson expansion that occurs as the high pressure feed passes through the membrane. Residue 24, for example, can have a temperature within the range of from about −40° C. to about 50° C. when exiting stage 12A.

To mitigate Joule-Thompson effects, the temperature of residue 24 obtained from stage 12A can be adjusted, (e.g., by heating), using a heat exchanger, such as variable heat exchanger 40, for example, to provide a stream characterized by a temperature within the range of from about 0° C. to about 60° C.

Additional methane is recovered by feeding stream 25 to stage 12B to obtain permeate 42, enriched in $CH_4$, and residue 44 ($CH_4$-depleted). While the target purity for stream 42 will change depending on the nitrogen concentration in the feed 16, the operating parameters of the system, and the desired methane recovery, as an example, when stream 16 contains 8 mol % $N_2$, we can expect that the $N_2$ content of stream 24 will be about 24 vol % and membrane stage 12B will be used to recover methane while reducing the $N_2$ concentration of permeate stream 42 down to about 12 vol %. Generally speaking, the ratio of the $N_2$ content of the feed 16 to the $N_2$ content of the product stream 38 is less than 4.

Residue 44 leaves stage 12B as the $N_2$-rich fraction, forming at least a portion of stream 46, a stream that can be removed as a waste stream, used as fuel or directed to a different operation, e.g., within the facility, that may require $N_2$-enriched gas.

Parameters such as feed pressure and permeate pressure that characterize the membrane(s) of stage 12B can be adjusted to achieve a desired methane recovery. Since permeate 42 is to be further purified in stage 14, no stringent constraints need to be placed on the purity of this fraction. In some implementations, however, the methane content of permeate 42 approaches (i.e., is within +/−80% of) the methane content of the feed.

A second stage compressor 48, can be employed to raise the pressure of permeate 42, generating stream 50, which can be at a pressure within the range of from about 150 to about 1400 psig.

Stream 50 is directed to gas aftercooler 52 to produce stream 54, which is processed in stage 14, employed to purify the recovered methane. For example when stream 54 is equal to 12% $N_2$ and stream 16 is 8% $N_2$, the objective of this membrane will be to achieve a purity of about 8% $N_2$ in stream 62 so that $N_2$ is not enriched in the feed beyond what can be purified to product specification in membrane 12A.

The two streams produced in stage 14 are permeate 62 and residue 64.

Optionally, the pressure of permeate 62 is increased using compressor 66 to produce stream 68, having a pressure within the range of from about 25 psig to about, e.g., about 300-1200 psig depending on the feed gas pressure. Stream 68 is directed to gas aftercooler 70) to generate stream 72, which is recycled back to the feed, in an arrangement in which stream 72 is combined with feed 16, for example. In specific embodiments, the nitrogen content of the recyclable stream derived from stage 14 is the same or about the same as that of the feed 16 (e.g., around 80% of the $N_2$ content of the feed 16). This prevents the $N_2$ enrichment of the feed 16.

In a different approach, compressor 66 is omitted and the recycled feed is compressed in a feed compressor, not shown in FIG. 1.

Residue 64 representing the N$_2$-rich (CH$_4$-depleted) fraction can be combined with residue 44 to form stream 46, described above. In other implementations, the residue streams can be handled individually (either as waste or for further use).

Embodiments described herein can be practiced or adapted to separations other than those involving CH$_4$—N$_2$ mixtures. Illustrative mixtures that could be separated by applying principles discussed above include but are not limited to ethane/methane, propane/ethane, and CO/N$_2$.

Computer Simulation Mass Balance

A computer simulation was conducted for a system such as that in FIG. 1, assuming the feed (stream 16) composition shown in Table 1. As seen in Table 1, methane is the major component, followed by nitrogen, ethane, propane, CO$_2$, and n-butane. The feed is assumed to contain no water (removal of moisture from the feed can be conducted in a multi-bed adsorption arrangement such as described above) or hydrogen sulfide. Other simulated process conditions are listed in FIG. 2.

TABLE 1

Properties of Feed Stream

| Label | Property | Feed |
|---|---|---|
| A | Vapor Fraction | 1.00 |
| B | Temperature [° F.] | 120 |
| C | Pressure [psig] | 1,100 |
| D | Molar Flow [MMSCFD] | 25.00 |
| E | Mass Flow [lb/hr] | 47,231 |
| F | HC Dew Point [° F.] | <empty> |
| G | H2O Dew Point [° F.] | <empty> |
| H | HHV [Btu/SCF] | 961 |
| I | Mole Fraction (CO$_2$) | 0.07% |
| J | Mole Fraction (Nitrogen) | 6.20% |
| K | Mole Fraction (Methane) | 91.05% |
| L | Mole Fraction (Ethane) | 2.51% |
| M | Mole Fraction (Propane) | 0.16% |
| N | Mole Fraction (i-Butane) | 0.00% |
| O | Mole Fraction (n-Butane) | 0.01% |

As seen in the results of the computer simulation, it is possible to obtain efficiently a methane product containing less than 3 mol % nitrogen while recovering 80% of the hydrocarbons thanks to this process.

While this invention has been particularly shown and described with references to preferred embodiments thereof, it will be understood by those skilled in the art that various changes in form and details may be made therein without departing from the scope of the invention encompassed by the appended claims.

What is claimed is:

1. A membrane separation process, comprising:
    processing a feed containing methane and nitrogen gas in a first membrane stage that is selective for methane over nitrogen to produce a first permeate and a first residue, the feed being natural gas having an N$_2$ content (in vol %), $F_{nitrogen}$, of no more than 10;
    collecting the first permeate as a methane-rich product, the methane-rich product having an N$_2$ content (in vol %), $P_{nitrogen}$;
    processing the first residue in a second membrane stage that is selective for methane over nitrogen to produce a second permeate and a second retentate;
    processing the second permeate in a third membrane stage that is selective for methane over nitrogen to obtain a third permeate and a third retentate;
    removing the second and third retentates as waste streams, or using the second and third retentates as fuel, or directing the second and third retentates to a different operation that requires N$_2$-enriched gas; and
    recycling the third permeate by combining it with the feed, wherein, a ratio of $F_{nitrogen}:P_{nitrogen}$ is less than 4.

2. The process of claim 1, further comprising adjusting a temperature of the first residue.

3. The process of claim 1, further comprising compressing one or more of the first, second and third permeate.

4. The process of claim 3, wherein each of the first, second, and third permeates is compressed.

5. The process of claim 1, wherein at least one of a second residue, obtained from the second membrane stage, and a third residue, obtained from the third membrane stage, is removed from the process as a nitrogen-rich fraction.

6. The process of claim 1, wherein the first membrane stage is operated at a stage cut within the range of from about 50% to about 95%.

7. The process of claim 1, wherein the first membrane stage is operated in radial cross flow mode.

8. The process of claim 1, wherein at least one of the first, second and third membrane stages comprises a membrane having a separation layer that includes a copolymer of dimethylsiloxane.

9. The process of claim 1, wherein the first residue is passed through a heat exchanger.

10. A membrane separation process, comprising:
    processing a feed containing methane and nitrogen gas in a first membrane stage that is selective for methane over nitrogen to produce a first permeate and a first residue, the feed being natural gas having an N$_2$ content (in vol %), $F_{nitrogen}$, of no more than 12%;
    collecting the first permeate as a methane-rich product, the methane-rich product having an N$_2$ content (in vol %), $P_{nitrogen}$;
    processing the first residue in a second membrane stage that is selective for methane over nitrogen to produce a second permeate and a second retentate;
    processing the second permeate in a third membrane stage that is selective for methane over nitrogen to obtain a third permeate and a third retentate;
    removing the second and third retentates as waste streams, or using the second and third retentates as fuel, or directing the second and third retentates to a different operation that requires N$_2$-enriched gas; and
    recycling the third permeate by combining it with the feed, wherein, a ratio of $F_{nitrogen}:P_{nitrogen}$ is less than 4.

11. The process of claim 1, wherein $P_{nitrogen}<3$ vol %.

12. The process of claim 1, wherein $F_{nitrogen}:P_{nitrogen}$ is less than 3 and at least 75 vol % of the methane in the feed is recovered in the methane-rich product.

* * * * *